United States Patent [19]

Fleischhacker

[11] Patent Number: 4,596,559
[45] Date of Patent: Jun. 24, 1986

[54] BREAK-AWAY HANDLE FOR A CATHETER INTRODUCER SET

[76] Inventor: John J. Fleischhacker, 16631 Meadowbrook La., Wayzata, Minn. 55391

[21] Appl. No.: 667,638

[22] Filed: Nov. 2, 1984

[51] Int. Cl.$^4$ .............................................. A61M 5/18
[52] U.S. Cl. ..................................... 604/170; 604/161
[58] Field of Search ............................... 604/160–162, 604/164, 166; 128/348

[56] References Cited

U.S. PATENT DOCUMENTS

| | | | |
|---|---|---|---|
| 4,166,469 | 9/1979 | Littleford | 604/164 |
| 4,306,562 | 12/1981 | Osborne | 604/164 |
| 4,402,685 | 9/1983 | Bühler | 604/164 |
| 4,411,654 | 10/1983 | Boarini et al. | 604/161 |
| 4,449,973 | 5/1984 | Luther | 604/161 |

Primary Examiner—Stephen C. Pellegrino
Assistant Examiner—Jerome R. Smith, Jr.
Attorney, Agent, or Firm—Herman H. Bains; Malcolm L. Moore; Conrad A. Hansen

[57] ABSTRACT

A tear-away introducer tool for a disposable introducer set used in introducing a catheter into a blood vessel comprises an elongate sheath having a pair of opposed splits in the proximal end thereof to define a pair of tabs. A handle is secured to the sheath and includes a pair of handle members, each comprising a pair of clamping elements which clamp the tabs of the sheath therebetween. The handle has opposed weakened portions which facilitate the tearing of the sheath along axial lines and the handle also facilitates manipulation of the introducer tool during the catheter introduction procedure.

3 Claims, 5 Drawing Figures

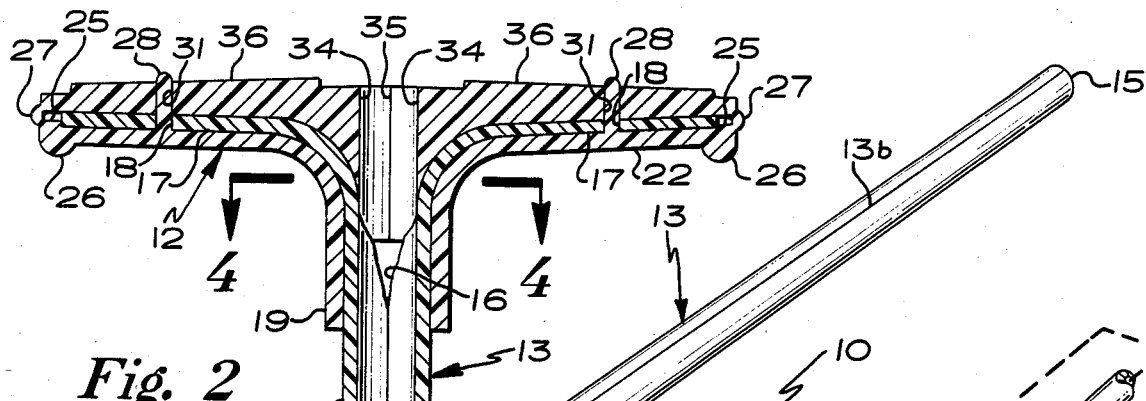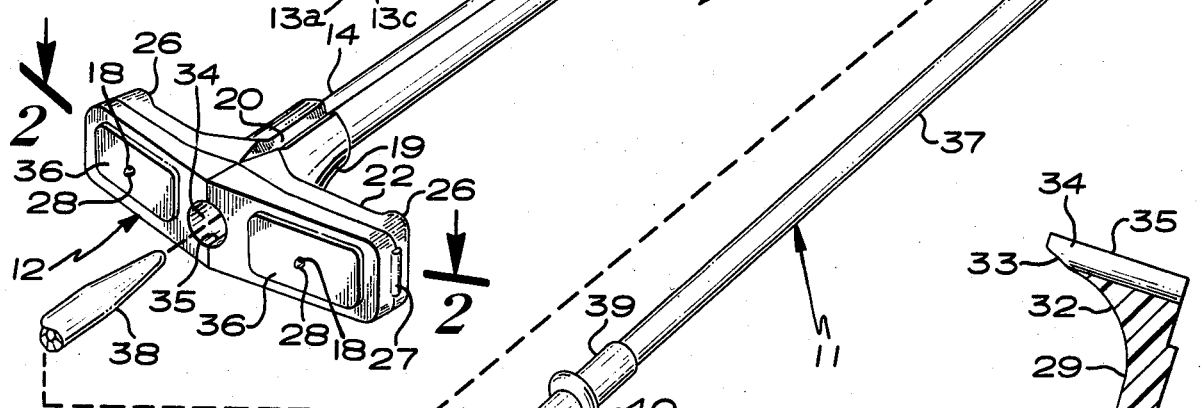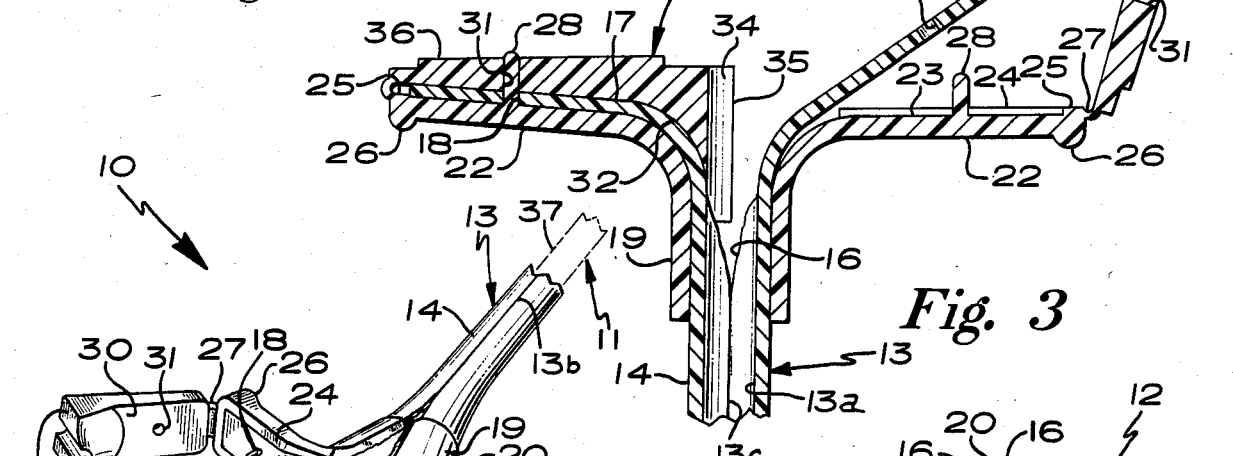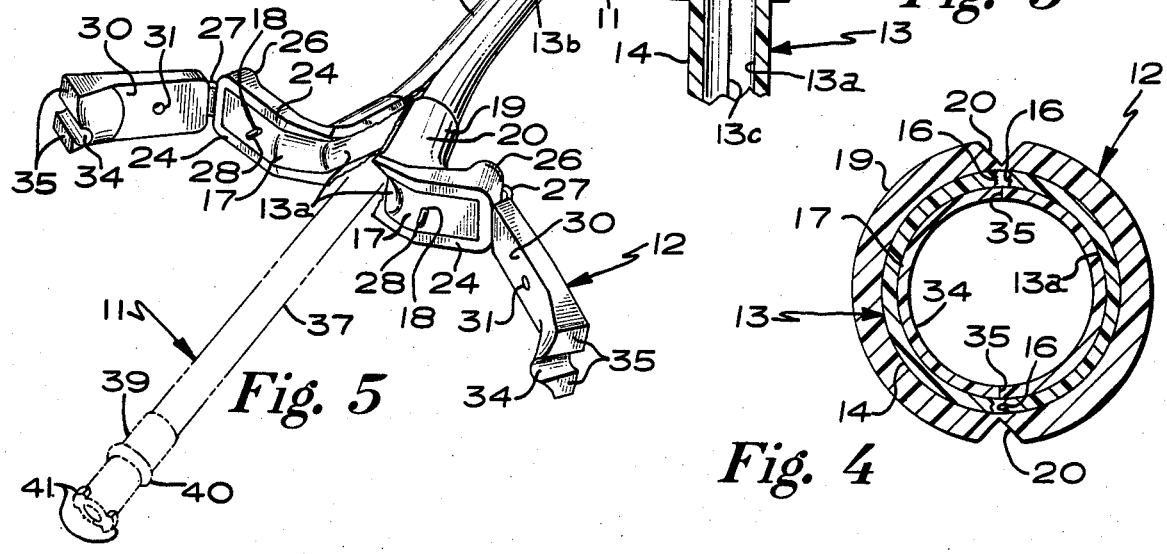

BREAK-AWAY HANDLE FOR A CATHETER INTRODUCER SET

This invention relates to a split type, break-away handle for a catheter introducer set used in introducing a catheter into a blood vessel.

BACKGROUND OF THE INVENTION

Commercial introducer sets have been developed which are used by doctors in introducing catheters into blood vessels. Such catheters may include a pacemaker lead which is typically introduced into the subclavian vein. Introducer sets include an introducer tool which comprises a sheath that is scored or split at its proximal end to permit splitting thereof longitudinally during the extraction of the introducer tool. Introducers of such construction are disclosed in U.S. Pat. Nos. 4,166,469 and 4,306,562, issued to Philip O. Littleford and Thomas A. Osborne, respectively. During the introduction procedure, a hollow vessel dilator and introducer tool are advanced into the vein over a guide wire. The surgeon obstructs the proximal end of the introducer tool to prevent air aspiration and blood loss when the vessel dilator and guide wire are withdrawn. In those commercial introducer sets having the introducer tool with a split proximal end, it is difficult to obstruct the proximal end because of the unevenness thereof. Further, the introducer tool is sometimes difficult to manipulate because of the floppy condition of the tabs defined by the split in the proximal end.

Some of the commercial introducer tear-away sheaths are formed of TFE Teflon, which has thermal setting properties that make it difficult to reliably and effectively bond other plastic materials to the sheath. However, many surgeons prefer Teflon sheaths because Teflon is so slippery and, in effect, is self-lubricating even though it is difficult to bond a suitable handle to such Teflon sheaths. Other manufacturers form the sheath of polyethylene, which can be remelted and bonded to a handle including knob-type handles. However, polyethylene does not provide the slippery smooth sensation characteristic of Teflon and preferred by a substantial number of doctors.

It is therefore a general object of this invention to provide a novel break-away handle for a tear-away self-lubricating TFE Teflon introducer sheath which enhances the manipulatability of the introducer sheath while providing a positive mechanical connection between the sheath and the handle.

It is another object of this invention to provide a split type, tear-away introducer tool for a catheter introducer set wherein the proximal ends of the introducer tool are provided with a handle which facilitates the manipulation of the tool and other components of the set during the introduction procedure.

Another object of this invention is to provide a split type tear-away introducer tool for a catheter introducer set which has a uniquely constructed handle that serves to stabilize the introducer tool and permits the surgeon to effectively obstruct the proximal end of the tool to thereby minimize the danger of air aspiration and blood loss when the vessel dilator and guide wire are removed.

A further object of this invention is to provide a catheter introducer set with a novel split type tear-away introducer tool having a handle which firmly grips the tabs at the proximal end of the introducer tool and thereby facilitates the tearing of the tool at the completion of the procedure. These and other objects of the invention are defined in the following specification.

FIGURES OF THE DRAWING

FIG. 1 is a perspective view of the novel introducer tool illustrated in conjunction with a vessel dilator.

FIG. 2 is a cross sectional view taken approximately along line 2—2 of FIG. 1 and looking in the direction of the arrows.

FIG. 3 is a fragmentary cross sectional view of the proximal end of the introducer tool with one of the upper clamping elements illustrated in an open condition and with one of the flaps in a raised position.

FIG. 4 is a cross sectional view taken approximately along line 4—4 of FIG. 2 and looking in the direction of the arrows.

FIG. 5 is a fragmentary perspective view of the proximal end of the introducer tool with the clamping elements of the handle in an open condition and with the introducer tool partially split.

DESCRIPTION OF THE PREFERRED EMBODIMENT

Referring now to the drawings and more specifically to FIG. 1, it will be seen that one embodiment of the novel introducer tool, designated generally by the reference numeral 10, is thereshown. In FIG. 1, a vessel dilator 11 is illustrated in exploded relation with respect to the introducer tool. The vessel dilator and introducer tool are components of an introducer set which includes a disposable syringe, a hollow hypodermic needle for use with the syringe, a wire guide, a disposable scalpel, as well as the vessel dilator and the introducer tool. These components will be described more fully hereinbelow.

The introducer tool 10 includes an elongate substantially cylindrical sheath 13 having a handle 12 affixed to the proximal end portion thereof. The sheath 13 is formed of a suitable plastic, preferably TFE Teflon, which is compatible with the body fluids and which has a proximal end 14 and a distal end 15. The proximal end 14 has a pair of opposed splits 16 therein which define a pair of tabs 17. Each tab 17 has an opening 18 therethrough, as best seen in FIGS. 2 and 3. The sheath 13 also has a pair of mechanically formed, longitudinally extending zones of reduced thickness defined by external scored longitudinal shallow grooves or indentations 13b and a pair of internal scored longitudinal shallow grooves or indentations 13c, each extending throughout the length of the sheath from one of the splits 16 therein.

The handle 12 includes a generally cylindrically shaped sheath engaging tubular portion 19 which engages and surrounds the proximal end portion of the sheath 13. The sheath engaging portion 19 has opposed longitudinally extending V-shaped grooves 20 therein, as best seen in FIG. 1. The grooves 20 facilitate the splitting of the handle in an axial direction in a manner to be described hereinbelow. It is pointed out that longitudinally arranged perforated portions could be used in lieu of the V-shaped grooves.

The handle 12 also includes a pair of handle members each comprising lower clamping elements 22 which are integral with the sheath engaging portion 19 and which project laterally outwardly therefrom. Each lower clamping element 22 is provided with a substantially flat recessed central portion 23 which defines a pair of side shoulders 24 interconnected by transverse end shoulder 25. The lower surface of each lower clamping element 22 is provided with a gripping bead 26 at its outer end, as best seen in FIG. 2. A locking pin 28 projects upwardly from the central portion of each lower clamping member and the outer end of each lower clamping member is provided with a hinge element 27. The gripping bead 26 facilitates gripping of the handle by a doctor.

The handle 12 also includes an upper clamping element 29 which is provided with a flat lower surface 30 and is integral with the hinge element 27 at one end thereof to permit swinging movement of the upper clamping member upwardly and outwardly relative to the lower clamping member. It will also be noted that each upper clamping member 29 has an opening 31 therethrough which accommodates the pin 28 on the associated lower clamping element 22.

The free end of the upper clamping element 29 has a conical shaped terminal guide element 32 integral therewith that terminates in a lower angled end 33. The guide element 32 of the upper clamping element 29 has a semi-circular surface 34 that terminates in vertical flat edges 35.

It will be seen that when the upper clamping element is in the closed position, as illustrated in FIGS. 1 and 2, each upper clamping element overlies the associated lower clamping element so that the edges 35 are disposed in confronting engaging relation with each other. The semi-circular surfaces 34 define a cylindrical opening or lumen in the handle which communicates with the interior 13a of the sheath 13. It will also be seen that the tabs 17 are positioned within the recessed central portion 23 of each lower clamping member to permit the locking pin 28 to project upwardly through the opening 18 in each tab. Thereafter when the upper clamping member is moved to the closed position, the locking pin 28 projects through the opening 31 in the upper clamping element. With this arrangement, the tabs 17 are securely clamped in place within the handle 12.

The vessel dilator 11 includes an elongate tubular portion 37 also formed of a suitable compatible plastic material which terminates in a tapered distal end 38. A tubular handle 39 is mounted on the proximal end of the tubular portion 37 and includes an annular stop member 40 which projects radially outwardly therefrom and which is adapted to engage the upper surface of the handle surrounding the opening defined by the semi-circular portions 34. The handle is also provided with a pair of laterally projecting ears 41 at its proximal end. The external diameter of the tubular portion 37 of the vessel dilator 11 is of a magnitude to pass through the opening defined in the handle 12 and through the interior 13a of the sheath 13. As pointed out above, a typical use of the introducer set is to introduce a pacemaker lead into the subclavian vein in a generally well-known procedure. The introducer set can be used to introduce a pacemaker lead into blood vessels other than the subclavian vein. It is also pointed out, however, that the introducer set could also be used to introduce other types of catheters into blood vessels.

The components of an introducer set include a disposable hypodermic syringe and needle, a guide wire, scalpel, introducer tool, and vessel dilator. The general procedure for introducing the catheter, such as a pacemaker lead, is well-known in the medical profession. After the vein has been entered with the hypodermic needle, the syringe is removed and a guide wire is introduced through the needle and inserted into the vein leaving a portion of wire exposed. Thereafter, the needle is removed from the wire and a small skin incision is made.

The vessel dilator 11 is then inserted through the handle 12 and through the interior 13a of sheath 13 of introducer tool 10. The tool 10 and vessel dilator 11 are advanced as a unit over the guide wire and through the skin incision into the vein. The introducer tool and vessel dilator are inserted until only approximately 6 centimeters of the unit are exposed. Thereafter, the vessel dilator 11 and the guide wire are withdrawn from the introducer tool and the surgeon will then place his thumb over the exposed opening in the handle 12 to prevent air aspiration and blood loss through the opening.

Thereafter, the catheter is inserted into the introducer tool 10 and advanced through the sheath 13 and into the vein. After the catheter has been well advanced, the introducer tool is withdrawn simultaneously splitting and pealing away the sheath 13 of the tool by gripping the handle elements and pulling the sheath apart. It will be appreciated that, by pulling the handle elements apart, the tubular portion of the sheath will also split along the elongated, reduced thickness portions 13b and 13c and, since the tabs of the sheath are clamped by the handle elements, the entire sheath will readily split.

This particular construction of the handle not only stabilizes the proximal end of the introducer tool for easy manipulation during the introduction procedure, but the handle also serves to facilitate splitting the sheath after introduction of the catheter into the blood vessel. Further, the orifice or opening defined by the clamping elements of the handle permits a surgeon to readily close the end of the introducer tool and minimize any likelihood of air aspiration and blood loss.

From the foregoing, it will be seen that I have provided a novel introducer tool which is not only a simple and inexpensive construction, but one which functions in a more efficient manner than any heretofore known comparable devices.

What is claimed is:

1. A split tear-away introducer tool for an introducer assembly including a vessel dilator, wire guide, needle, syringe and the like for use in introducing a catheter into a blood vessel, comprising:

an elongate cylindrical sheath having a distal end and a proximal end, said proximal end having a pair of splits therein defining a pair of tabs, each tab having an opening therein, a handle including a tubular portion engaging the proximal end of said sheath body to mount said handle thereon, a pair of lower clamping elements integral with said tubular portion and extending laterally outwardly therefrom, a pair of upper clamping elements, hinge means connecting the outer end of each lower clamping member with the associated upper clamping member to permit swinging movement of the latter about an axis lying in a plane disposed substantially normal to the plane in which the longitudinal axis of the elongate sheath lies, each upper clamping member being swingable between open and closed positions, each of said upper clamping elements, when in the closed position, overlying the associated lower clamping element and clamping one of said tabs therebetween, each upper clamping member having an opening therein, each lower clamping member having a pin thereon projecting through the opening in a tab into the opening in the associated upper clamping member to thereby lock the tab to the handle, a pair of arcuate guide elements each being integral with one end of one of said upper clamping elements whereby said guide elements define a lumen aligned in communicating relation with the interior of the sheath body when said upper clamping elements are in the closed position and being of a size to accommodate a vessel dilator, catheter, and the like when said upper clamping elements are in the closed position, said handle members of said handle, when pulled apart, facilitating tearing of said sheath axially from said slits therein.

2. The introducer tool as defined in claim 1 wherein said tubular portion of said handle has opposed weakened portions, each weakened portion being disposed in overlying aligned relation with one of said splits in the proximal end of the sheath and aligned with the weakened wall of the sheath.

3. The introducer tool as defined in claim 1 wherein said guide elements on said upper clamping elements have flat edges which are disposed in confronting engaging relation with each other when the upper clamping elements are in the closed position.

* * * * *